United States Patent
Thies, Jr.

[11] Patent Number: 6,007,124
[45] Date of Patent: Dec. 28, 1999

[54] INTRAVENOUS BAG AND BOTTLE HOLDER

[76] Inventor: Kenneth K. Thies, Jr., 5250 Blockhouse Rd., Fredonia, N.Y. 14063

[21] Appl. No.: 08/963,008

[22] Filed: Nov. 3, 1997

Related U.S. Application Data

[60] Provisional application No. 60/030,868, Nov. 13, 1996.

[51] Int. Cl.$^6$ .............................. B65G 7/12; A61G 12/00
[52] U.S. Cl. .......................... 294/26; 294/142; 248/121; 248/318
[58] Field of Search ................ 294/2, 19.1, 24, 294/26, 27.1, 15, 142, 158; 248/121, 122.1, 125.8, 303, 304, 311.3, 318, 339

[56] References Cited

U.S. PATENT DOCUMENTS

| | | | |
|---|---|---|---|
| 1,877,727 | 9/1932 | McClarkey et al. | 248/303 |
| 2,065,012 | 12/1936 | Mulford | 248/318 |
| 2,739,832 | 3/1956 | Thorpe | 294/19.1 |
| 2,882,084 | 4/1959 | Eatinger | 294/26 |
| 3,038,752 | 6/1962 | Bergman | 294/19.1 |
| 3,923,279 | 12/1975 | Gresley et al. | 248/318 |
| 3,985,382 | 10/1976 | Wheeler | 294/50.6 |
| 4,047,687 | 9/1977 | Turner | 248/318 |
| 4,094,391 | 6/1978 | Ratchford | 190/18 |
| 4,153,286 | 5/1979 | Piper et al. | 294/19 |
| 4,306,662 | 12/1981 | Sciortino et al. | 248/318 |
| 4,899,050 | 2/1990 | Cianflone | 200/331 |
| 4,955,647 | 9/1990 | Alfredson | 294/14 |
| 5,029,921 | 7/1991 | Houghton et al. | 294/26 |
| 5,222,946 | 6/1993 | Kamen | 248/121 |
| 5,351,365 | 10/1994 | Hauck | 16/114 |
| 5,582,377 | 12/1996 | Quesada | 248/303 |

*Primary Examiner*—Dean Kramer
*Attorney, Agent, or Firm*—Lovercheck and Lovercheck

[57] ABSTRACT

A tool for handling intravenous supplies packaged in containers such as bottles and bags. The tool has an engaging end which both engages a fixture to support the tool in a working position, and engages an intravenous container to support it in the working position. The tool has a handle and a shaft extending between the engaging end and the handle. The shaft is long enough to reach support fixtures and shaped to hang without contacting the intravenous container. The handle is shaped to accommodate a user's hand

26 Claims, 2 Drawing Sheets

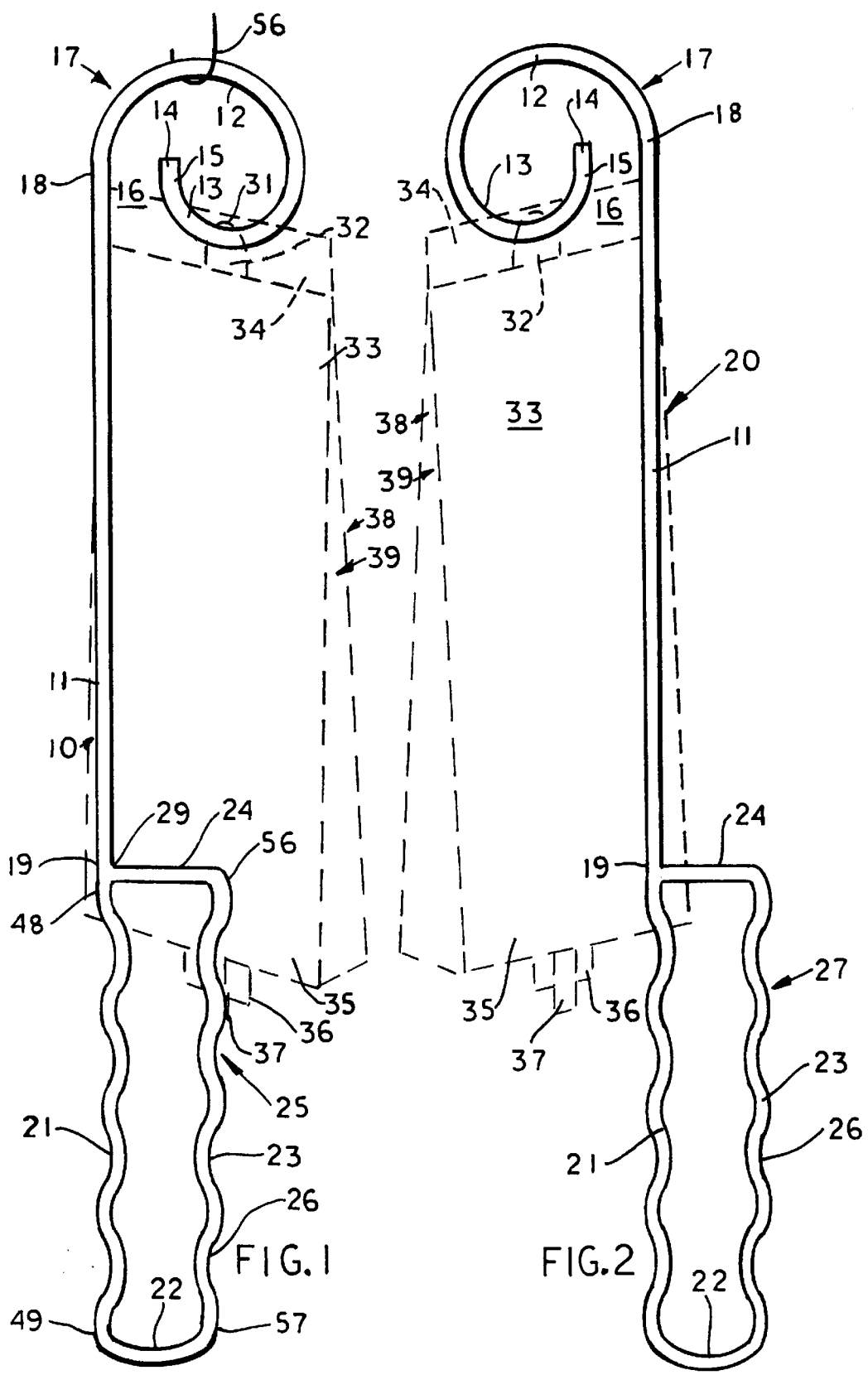

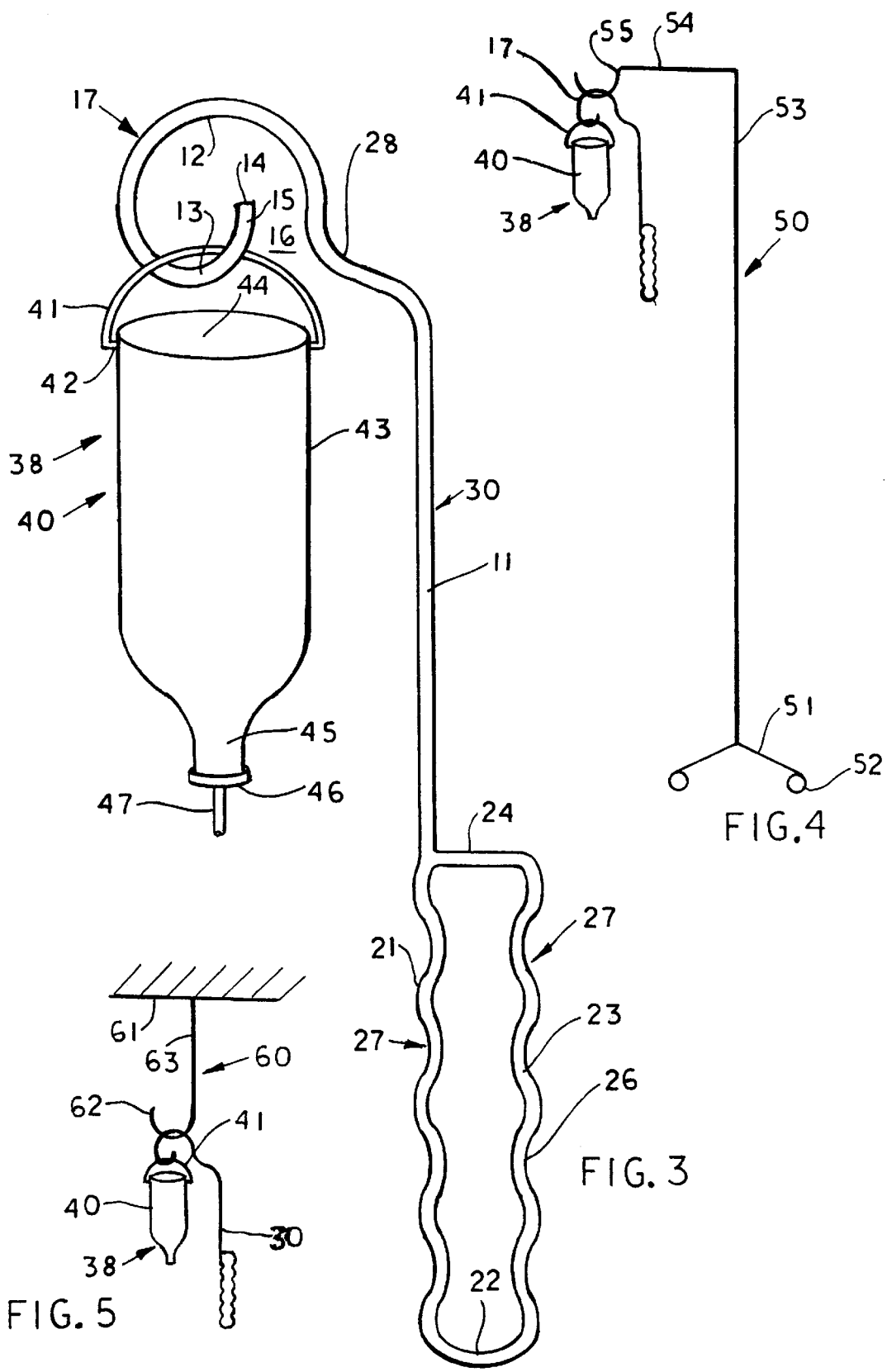

INTRAVENOUS BAG AND BOTTLE HOLDER

This application claims the benefit of U.S. Provisional Application Ser. No. 60/030,868 filed Nov. 13, 1996.

BACKGROUND OF THE INVENTION

This invention relates generally to the handling and supporting of intravenous bags and bottles during medical treatment and deals more particularly with a tool or a hanger which may be used to support an intravenous bag or bottle by engaging a ceiling supporting hook or a hook at the top of a portable intravenous stand thus supporting the intravenous bag or bottle thereon.

Although intravenous supplies are commonly hung from intravenous hooks fixed to ceilings, or supported by intravenous hooks attached at the top of portable wheeled intravenous stands, it is difficult to reach these hooks due to the height of their suspension above the floor.

Typically, the intravenous bag is suspended on a hook by passing a hole in the top margin of the bag over the hook. The intravenous bottle is typically suspended on a bail or handle affixed adjacent to its upper end. The bail is adapted to placed over the hook.

Since the intravenous supplies must be positioned well above the patient to be effective, the hook supporting the supplies is normally positioned too high for average height persons to reach by hand. Therefore, substantial difficulty is encountered in placing intravenous supplies on and removing them from the hook.

Applicant is aware of the following U.S. Pat. Nos. 2,882,084; 4,094,391; 4,153,286; 4,899,050; 4,955,647; 5,029,921; and 5,351,365.

SUMMARY OF THE INVENTION

The intravenous bag and bottle hanger is provided to ease the task in hanging intravenous supplies. Intravenous supplies are packaged in various ways, most commonly in bags and bottles provided with hanging structure at a first end and dispensing structure at a second end. The hanger has an opening on one end which allows the hanging structure of an intravenous bag or bottle to be placed over the end of the hanger and supported on the hanger and then the hanger itself is hung on the ceiling supported intravenous hooks or on a hook supported adjacent the top of a portable intravenous stand to support the intravenous supply.

The shaft is long enough to provide a convenient reach to the ceiling supported intravenous hooks and the hooks adjacent the top of the portable intravenous stand. In another embodiment, the shaft is offset away from the handle, and the end structure extends away from the handle side of the shaft to more readily accommodate an intravenous bottle, a larger size intravenous bag, or other intravenous supplies.

The end structure receives the supporting structure of the intravenous supplies to support the supplies on the hanger. The end structure also receives the overhead fixture to support said hanger in a working position so the intravenous supplies can be effectively administered to the patient.

The end structure may be generally circular and receive the fixture against a first arcuate portion thereof. The supporting structure of the intravenous supplies, for example, a hole through the top margin of an intravenous bag, or the bail of an intravenous bottle, are received against a second arcuate portion of the end structure.

The end structure ends in a rounded tip which is so constructed that it will not puncture intravenous bags when impacted thereon. The tip of the end structure is spaced from the shaft providing an area through which the top margin of t he intravenous bag or the bail of an intravenous bottle, or the engaging portion of another intravenous supply may pass to be supported on the end structure of the hanger.

The end structure may be made with a first arcuate portion having a first r adius and a second arcuate portion of a second radius. By making the second radius smaller than the first radius, the space between the shaft and the top is provided. Between the end of the second radius and the tip may be provided a straight portion lying generally parallel to the shaft and made long enough to assure support of the intravenous supplies thereon which the hanger is being hung or removed from the fixture.

The handle provides a good grip and the arm is of sufficient length to reach the ceiling or portable intravenous hooks. More than one bag or bottle may be hung on the hanger providing flexibility in the use of the handle enhanced by the hanger which allows for fast hook up of intravenous supplies, including bags or bottles.

The handle may be made from an end portion of the elongate shaft having a first end and a second end. A first portion may be spaced from and extend generally coextensive with and parallel to the end portion. The first portion will have a first end adjacent the first end of the end portion, and a second end adjacent the second end of the end portion. A second portion may extend between the first end of the end portion and the first end of the first portion. A third portion may extend between the second end of the end portion and the second end of the first portion. The end portion, the first portion, the second portion and the third portion generally encloses a rectangular space. The end portion and the first portion may be shaped to accommodate a hand gripping the handle. A method of handling intravenous supplies is provided to hang, support and remove intravenous supplies. The supplies must be suspended well above a patient to be properly administered. The method includes supplying a fixture, supplying a hanger, and supplying intravenous supplies. The intravenous supplies are supported on the hanger, and the hanger is suspended on the fixture. When the intravenous supplies have been delivered, the hanger may be removed from the fixture, the intravenous supplies may be restocked on the hanger as desired, and the hanger may be rehung on the fixture.

The principle goal of the present invention is to provide a tool which facilities the hanging of intravenous bags and bottles.

It is a further object of the present invention to provide a tool as adapted to support intravenous supplies on an overhead hook or portable intravenous structure or the like.

It is another object of the present invention to provide a hook which is simple in construction, economical to manufacture, which may be quickly and easily used and which is adapted for use with hooks located at various heights, and simple and efficient to use.

With the above and other objects in view, the present invention consists of the combination and arrangement of parts hereinafter more fully described, illustrated in the accompanying drawing and more particularly pointed out in the appended claims, it being understood that changes may be made om the form, size, proportions and minor details of construction without departing from the spirit or sacrificing any of the advantages of the invention

BRIEF DESCRIPTION OF THE DRAWING(S)

FIG. 1 is a side view showing a tool constructed according to the present invention being used to support an intravenous bag on a hook.

FIG. 2 is a side view showing a second embodiment of a tool constructed according to the present invention being used to support an intravenous bag on a hook.

FIG. 3 is a side view of a third embodiment of a tool according to the present invention being used to support an intravenous bottle on a hook.

FIG. 4 is a portable intravenous stand with a hook adjacent its upper end and showing a tool being used to support an intravenous bottle on the hook.

FIG. 5 is a ceiling mounted intravenous supply support hook and a tool being used to support an intravenous bottle thereon.

DESCRIPTION OF THE PREFERRED EMBODIMENTS

Now with more particular reference to the drawings, intravenous supply bag and bottle hanger 10 is shown in FIG. 1, a second embodiment of hanger 20 is shown in FIG. 2, and a third embodiment of hanger 30 is shown in FIG. 3. Intravenous supplies 38 may be packed in bags 39 or bottles 40.

Hanger 10 has elongate shaft 11, end structure 17 at first end 18 of shaft 11, and handle 25 at second end 19 of shaft 11.

As shown in FIG. 1, hanger 10 has shaft 11 that is long enough to provide a convenient reach to supporting hooks 56. Supporting hooks 56 may be ceiling supported intravenous hook 60 as shown in FIG. 5, or it may be hook 55 adjacent the top of portable intravenous stands 50 as shown in FIG. 4.

In a second embodiment, handle 27 of hanger 20 shown in FIG. 2 extends outwardly from shaft 11 on the side opposite from the side that the end structure 17 extends outwardly from shaft 11 to provide less obstruction to the intravenous supplies support on second arcuate portion 13 of hanger 20.

In a third embodiment, shaft 11 of hanger 30 is shown in FIG. 3, has offset 28 which will support the intravenous supplies away from shaft 11 and handle 27. In this structure as shown in FIG. 3, end structure 17 extends away from handle 27 side of shaft 11 to more readily accommodate intravenous supplies 38.

End structure 17 has entry area 16 which allows the hanging structure of intravenous bag 39, bottle 40 or other intravenous supplies 38 to be placed over the end of hanger 10,20,30 and supported on hanger 10,20,30 along second arcuate portion 13. Hanger 10,20,30 itself is hung on ceiling intravenous hooks 60 or on hooks 55 supported adjacent the top of portable intravenous stands 50. Hanger 10,20,30 engages hooks 56 along first arcuate portion 12 to support the intravenous supplies in a working position.

End structure 17 receives the supporting structure of intravenous supplies 38 to support the supplies on hanger 10,20,30. End structure 17 also receives the overhead fixture to support hanger 10,20,30 in a working position so the intravenous supplies can be effectively administered to the patient.

End structure 17 ends in rounded tip 14 which is so constructed so that it will not puncture intravenous bags when impacted thereon. Tip 14 of end structure 17 is spaced from the shaft 11 providing an area 16 through which upper margin 34 of intravenous bag 39 or bail 41 of intravenous bottle 40, or the engaging portion of another intravenous supply 38 may be pass through entry area 16 to be supported on the end structure of the hanger.

End structure 17 may be made with first arcuate portion 12 having a first radius and second arcuate portion 13 having a second radius. By making the second radius smaller than the first radius, entry area 16 between shaft 11 and tip 14 is provided. Between the end of the second radius and tip 14 may be provided straight portion 15 lying generally parallel to shaft 11 and being long enough to assure support of intravenous supplies 38 thereon while hanger 10 is being hung or removed from hooks 56.

Handle 25,27 provides a good grip for the engaging hand of a person. Shaft 11 is of sufficient length to reach ceiling mounted hooks 60, or portable intravenous stand hooks 55. More than one bag or bottle may be hung on hanger 10,20,30 providing for flexibility in use under many conditions. The reach of the user is greatly enhanced by the hanger which allows for fast hook up of intravenous supplies of bags or bottles.

Handle 25,27 may be made from an end portion of elongate shaft 11. Handle 25,27 may have first portion 21 generally forming an extension of shaft 11. Second portion 23 may be spaced from and extend generally coextensive with and parallel to first portion 21. Second portion 23 will have first end 56 adjacent to first end of first portion 21, and second end 57 adjacent the second end of first portion 21. Third portion 24 may extend between first end 48 of first portion 21 and first end 56 of second portion 23. Fourth portion 22 may extend between second end 49 of first portion 21 and second end 57 of second portion 21. The first, second, third and fourth portions generally enclose a rectangular space. The first portion and third portion may be attached to joint 29. First portion and second portion may be shaped at 26 to accommodate a hand gripping handle 25.

Intravenous supplies 38 are packaged in various ways, most commonly in flexibility bags 39 and hard bottles 40. Intravenous supplies 38 however packaged, are provided with a hanging structure at a first end and a dispensing structure at second end.

Intravenous bag 39 has upper margin 34 that is gathered together and has hole 32 therethrough which may be used to support intravenous bag 39. Body 33 of intravenous bag 39 holds the fluid to be provided to the patient. Upper margin 34 has top edge 31. At the lower end of body 33 is lower margin 35 which contains plug 36 through which intravenous tube 37 may be provided to deliver fluid to a patient.

Intravenous bottle 40 has handle or bail 41 which is rotatably supported in recesses 42 in body 43 of intravenous bottle 40. Intravenous bottle 40 has top 44 at the upper end of body 43, and neck 45 at the lower end of body 43. Neck 45 is closed with plug 46 through which intravenous tube 47 may extend to deliver fluid to a patient.

Portable intravenous stand 50 may be provided having base 51 supporting wheels 52. Base 51 may also support upright member 53 having bracket 54 adjacent its upper end. At least one hook 55 will be supported on bracket 54 to support hanger 10,20,30 in a working position.

Ceiling mounted hook 60 will include bracket 63 affixed to ceiling 61. Bracket 63 will support hook 62 to support hanger 10,20,30 in a working position.

A method of handling intravenous supplies is provided to hang, support and remove intravenous supplies. The supplies must be suspended well above a patient to be properly administered. The method includes supplying a fixture, supplying a hanger, and supplying intravenous supplies. The intravenous supplies are supported on the hanger, and the hanger is suspended on the fixture. When the intravenous supplies have been delivered, the hanger may be removed from the fixture, the intravenous supplies may be restocked on the hanger as desired, and the hanger may be rehung on the fixture.

Hanger 10 may be fabricated of stainless steel for durability, appearance and sanitary purposes. Although not as durable, the hanger may also be fabricated of plastic for a throw-away version. The end structure 17 may be provided with an entry area 16 having a two inch opening to facilitate the hanging of intravenous supplies on ceiling hooks or portable intravenous stands. Multiple bags may be hung with a stainless steel hanger. Puncture of the intravenous bag is prevented by a round tip 14 and intravenous bags may be retained on the hook by a straight end 15 that may be approximately 3/4" long.

The opening guides the bag or bottle onto the end structure and allows a fast, smooth hook-up for the intravenous supply. The handle design facilitates a good grip and provides added height. The hanger shown in FIG. 3 was designed to accommodate intravenous supply bottles. The hook is offset, the amount of the offset may be approximately 1–1/4" to accommodate the bottle and the hook is reversed from FIG. 1.

The foregoing specification sets forth the invention in its preferred, practical forms but the structure shown is capable of modification within a range of equivalents without departing from the invention which is to be understood is broadly novel as is commensurate with the appended claims.

The embodiments of the invention in which an exclusive property or privilege is claimed are defined as follows:

1. A tool for handling intravenous supplies of the type to be suspended from a fixture;

said tool comprising;

a handle adapted to be gripped in the hand;

a elongated shaft extending from the handle;

said elongated shaft being offset along its length so said tool will hang without engaging on said intravenous supplies while in use;

an end structure for receiving said fixture against a first surface and for receiving said intravenous supplies against a second surface.

2. The tool recited in claim 1 wherein said end structure is generally circular and said fixture is received against a first arcuate portion and said intravenous supplies are received against a second arcuate portion.

3. The tool recited in claim 1 wherein said end structure has an opening through which an engaging portion of the fixture and the intravenous supplies may pass.

4. The tool recited in claim 1 wherein said end structure has a first arcuate portion of a first radius, and a second arcuate portion of a second radius;

said second radius being smaller than said first radius.

5. The tool recited in claim 1 wherein said end structure ends in a straight portion generally parallel to said shaft.

6. The tool recited in claim 1 wherein a tip of said end structure is rounded.

7. A tool for handling intravenous supplies of the type to be suspended from a fixture;

said tool comprising;

said handle adapted to be gripped in the hand;

an elongate shaft extending from the handle; and, an end structure for receiving said fixture against a first surface and for receiving said intravenous supplies against a second surface;

said handle comprises an end portion of said elongate shaft;

said end portion having a first end and a second end;

a first portion spaced from and generally coextensive with said end portion and having a first end and second end;

a second portion extending between the first end of said end portion and said first end of said portion;

a third portion extending between the second end of said end portion and said second end of said first portion.

8. The tool recited in claim 7 wherein said first portion and said second portion are shaped to accommodate said hand gripping said handle.

9. The tool recited in claim 7 wherein said end structure is generally circular and said fixture is received against a first arcuate portion and said intravenous supplies are received against a second arcuate portion.

10. The tool recited in claim 7 wherein said end structure has an opening through which an engaging portion of the fixture and the intravenous supplies may pass.

11. The tool recited in claim 7 wherein said end structure has a first arcuate portion of a first radius, and a second arcuate portion of a second radius;

said second radius being smaller than said first radius.

12. The tool recited in claim 7 wherein said end structure ends in a straight portion generally parallel to said shaft.

13. The tool recited in claim 7 wherein a tip of said end structure is rounded.

14. A hanger for intravenous supplies of the type to be suspended from a fixture;

said hanger comprising an elongate shaft;

said elongated shaft being offset along its length so said hanger will hang without engaging on said intravenous supplies while in use;

a handle at a first end of the shaft;

an end structure at a second end of the shaft;

said end structure engagable on said fixture to support said hanger thereon;

said intravenous supplies engagable on said end structure to support said intravenous supplies thereon.

15. The hanger recited in claim 14 wherein said end structure is generally circular and said fixture is received against a first arcuate portion and said intravenous supplies are received against a second arcuate portion.

16. The hanger recited in claim 14 wherein said end structure has an opening through which an engaging portion of the fixture and the intravenous supplies may pass.

17. The hanger recited in claim 14 wherein said end structure has a first arcuate portion of a first radius, and a second arcuate portion of a second radius;

said second radius being smaller than said first radius.

18. The hanger recited in claim 14 wherein said end structure ends in a straight portion generally parallel to said shaft.

19. The hanger recited in claim 14 wherein a tip of said end structure is rounded.

20. A hanger for intravenous supplies of the type to be suspended from a fixture;

said hanger comprising an elongate shaft;

a handle at a first end of the shaft;

an end structure at a second end of the shaft;

said end structure engagable on said fixture to support said hanger thereon;

said intravenous supplies engagable on said end structure to support said intravenous supplies thereon;

said handle comprises an end portion of said elongate shaft;

said end portion having a first end and a second end; a first portion spaced form and generally coextensive with said end portion and having a first end and a second end;

a second portion extending between the first end of said end portion and said first end of said first portion;

a third portion extending between the second end of said end portion and said second end of said first portion.

21. The hanger recited in claim 20 wherein said end portion and said first portion are shaped to accommodate said hand gripping said handle.

22. The hanger recited in claim 20 wherein said end structure is generally circular and said fixture is received against a first arcuate portion and said intravenous supplies are received against a second arcuate portion.

23. The hanger recited in claim 20 wherein said end structure end structure has an opening through which an engaging portion of the fixture and the intravenous supplies may pass.

24. The hanger recited in claim 20 wherein said end structure has a first arcuate portion of a first radius, and a second arcuate portion of a second radius;

said second radius being smaller than said first radius.

25. The hanger recited in claim 20 wherein a tip of said end structure is rounded.

26. The hanger recited in claim 20 wherein a tip of said end structure is rounded.

* * * * *